United States Patent
Lin et al.

(10) Patent No.: US 6,762,151 B2
(45) Date of Patent: Jul. 13, 2004

(54) METHODS OF AND COMPOSITIONS FOR PLANT DEFOLIATION

(75) Inventors: Hengchen Lin, Overland Park, KS (US); James R. Bloomberg, Overland Park, KS (US); Brent D. Philbrook, Holt, MO (US)

(73) Assignee: Bayer Crop Science LP, Pittsburgh, PA (US)

( * ) Notice: Subject to any disclaimer, the term of this patent is extended or adjusted under 35 U.S.C. 154(b) by 0 days.

(21) Appl. No.: 10/023,100

(22) Filed: Dec. 17, 2001

(65) Prior Publication Data

US 2003/0158041 A1 Aug. 21, 2003

(51) Int. Cl.[7] .......... A01N 47/44; A01N 47/30; A01N 57/04; A01N 43/828
(52) U.S. Cl. .......... 504/127; 504/139; 504/148; 504/165; 504/170; 504/173; 504/343
(58) Field of Search .......... 504/127, 139, 504/148, 165, 170, 173, 343

(56) References Cited

U.S. PATENT DOCUMENTS

| | | | | |
|---|---|---|---|---|
| 4,594,092 A | * | 6/1986 | Speltz et al. | 71/77 |
| 4,639,268 A | * | 1/1987 | Arotin et al. | 71/105 |
| 4,804,780 A | * | 2/1989 | Speltz et al. | 564/104 |
| 4,944,788 A | * | 7/1990 | Speltz et al. | 71/88 |
| 5,175,365 A | * | 12/1992 | Arotin et al. | 564/105 |

* cited by examiner

Primary Examiner—S. Mark Clardy
(74) Attorney, Agent, or Firm—Richard E. L. Henderson; Joseph C. Gil

(57) ABSTRACT

A method of defoliating plants includes applying to plants an effective amount of a first active ingredient selected from the group consisting of substituted nitroguanidine and cyanoguanidine compounds of the formula:

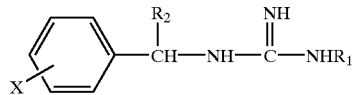

wherein $R_1$ is $NO_2$ or $CN$; $R_2$ is $CH_3$, $C_2H_5$, $CF_3$, $n-C_3H_7$, $CH_2OCH_3$ or $CH_2CH=CH_2$; X is hydrogen, o-F, m-F, p-F, m-$OCH_3$, m-OH or p-Cl; and the salts, tautomers and optical isomers thereof; an effective amount of a second active ingredient and optionally, an adjuvant.

8 Claims, No Drawings

METHODS OF AND COMPOSITIONS FOR PLANT DEFOLIATION

FIELD OF THE INVENTION

This invention relates to methods of and compositions for defoliating plants and/or for decreasing regrowth. More particularly, the invention relates to methods of defoliating plants and/or decreasing growth comprising applying to plants a guanidine compound. The invention also relates to compositions comprising a guanidine compound.

BACKGROUND OF THE INVENTION

Methods of controlled defoliation of plants and inhibition of regrowth after defoliation have important agricultural uses. For example, cotton defoliation prior to harvest eliminates the main source of stain and trash, resulting in better grade cotton. Stain from poorly defoliated plants or regrowth and moisture from green tissue can result in loss of cotton quality. It is desirable that growth of new leaves, referred to as regrowth, be inhibited after defoliation Examples of compounds that are commonly used as cotton defoliants include S,S,S-tributyl phosphorotrithioate, also known as tributifos and available under the trade name Def-6®, 1-phenyl-3-(1,2,3-thiadiazol-5-yl)urea, also known as thidiazuron and available under the trade name Dropp®, dimethipin and sodium chlorate. Unfortunately, many commonly used cotton defoliants require high application levels. Further, it is desirable that dead leaves drop off the cotton plant, however, in many instances the application of commonly used cotton defoliants results in leaves which are dead but not dropped from the plants.

Thidiazuron provides regrowth control as will as some defoliation. However, in order to attain a suitable level of defoliation tributifos, which causes defoliation but has little regrowth control, is usually applied along with the thidiazuron. It would be convenient if growers could apply a single active ingredient to plants, particularly cotton, which would provide both defoliation and regrowth control.

Speltz et al., U.S. Pat. Nos. 4,594,092, 4,804,780, and 4,944,788, teach guanidine compounds represented by the formula

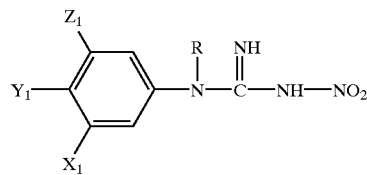

wherein $X_1$ is $COCH_3$, halogen, CN, $CH_2$ CN, $C(OH)_2$ $CF_3$, $OCHF_2$, $OCF_3$, $CH_3$, $CF_3$, $NO_2$, $OCF_2CHF_2$, $OCH_3$, $N(CH_3)_2$, or $CH_2$ $OR_3$ where $R_3$ is H or $CH_3$; $Y_1$ is H, halogen, $CH_3$; $Z_1$ is H, $CH_3$, halogen, $OCH_3$ or $CF_3$; R is H or $CH_3$; with the provisos that when $X_1$ is $CH_3$, $OCH_3$, F, Cl or Br and R is H, then $Y_1$ and $Z_1$ cannot both be hydrogen; and when $X_1$ is Cl and $Z_1$ and R are each hydrogen, then $Y_1$ cannot be methyl; and the salts or tautomers thereof;

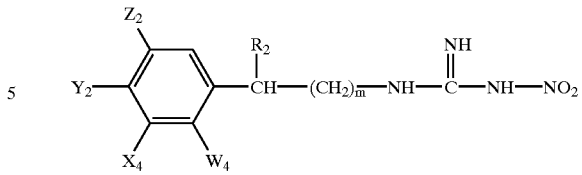

wherein $X_2$ is H, OH, straight or branched $C_1$–$C_4$ alkoxy, halogen, $OCF_3$, $CF_3$, straight or branched $C_1$–$C_4$ alkyl or $Y_2$ is H or F; $Z_2$ is F, H, $CH_3$ or $OCH_3$; $W_2$ is H or F; m is an integer of 0, 1, or 2; $R_2$ is H, $CH_3$, $C_2$ $H_5$ or $CF_3$; with the provisos that when m is 0 and $R_2$ is $CH_3$, then $W_2$, $X_2$, $Y_2$ and $Z_2$ cannot all be hydrogen; and when m is 1, then $R_2$, $W_2$, $X_2$, $Y_2$ and $Z_2$ cannot all be hydrogen; and the salts or tautomers thereof;

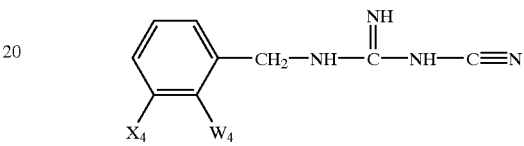

wherein $W_4$ is H or F and $X_4$ is straight or branched $C_1$–$C_4$ alkoxy, straight or branched $C_1$–$C_4$ alkyl or F; with the provisos that when $W_4$ is F, $X_4$ is H; and the salts or tautomers thereof. Speltz et al. teach the use of the compounds for inducing a cytokinin-like response in ornamental and crop plants and for increasing crop yield.

Arotin et al., U.S. Pat. Nos. 4,639,268 and 5,175,365, disclose substituted nitroguanidine or cyanoguanidine compounds of the structure:

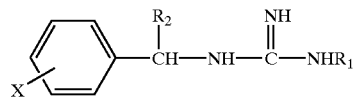

wherein $R_1$ is $NO_2$ or CN; $R_2$ is n-$C_3H_7$, $CH_2OCH_3$ or $CH_2CH=CH_2$; X is hydrogen, o-F, m-F, p-F, m-$OCH_3$, m-OH or p-cl; the salts, tautomers and optical isomers thereof and the (+) or (—)-isomers of compounds having the above structure, wherein $R_1$ and X are as described and $R_2$ is $CH_3$, $C_2H_5$ or $CF_3$, for use in preemergence control of undesirable broadleaf weeds and grass plants and in defoliating and/or desiccating plants. Arotin et al. teach that the substituted nitroguanidine or cyanoguanidine compounds may be used in combination with defoliants including N-(substituted phenyl)-N-1,2,3-thiadiazole-5-yl ureas; tributyl phosphorotrithioate; sodium chlorate; 2-(2-imidazolin-2-yl)quinolines; 2-(2-imidazolin-2-yl)-pyridines; O,O,O',O'-tetraethyl dithiopyrophosphate; and 2,1,3-benzothiadiazole-dicarbonitriles.

There is a need for defoliant compositions which can be used at low application levels. There is also a need for methods of inhibiting regrowth of plants, particularly regrowth of cotton leaves, after defoliation.

SUMMARY OF THE INVENTION

Accordingly, it is an object of the present invention to obviate problems of the prior art.

It is a further object of the present invention to provide methods of defoliating and/or inhibiting regrowth in plants.

It is a another object of the present invention to provide methods of defoliating and/or inhibiting regrowth in plants which can utilize low application levels of active ingredients.

It is a yet another object of the present invention to provide compositions for defoliating and/or inhibiting regrowth in plants, particularly cotton plants.

It is a further object of the present invention to provide methods of removing a source of stain and trash from cotton.

According to one aspect of the invention there are provided methods of defoliating plants comprising applying to plants an effective amount of a first active ingredient selected from the group consisting of substituted nitroguanidine and cyanoguanidine compounds of the formula:

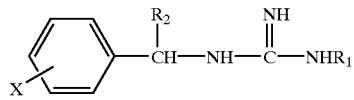

wherein $R_1$ is $NO_2$ or CN; $R_2$ is $CH_3$, $C_2H_5$, $CF_3$, n-$C_3H_7$, $CH_2OCH_3$ or $CH_2CH=CH_2$; X is hydrogen, o-F, m-F, p-F, m-$OCH_3$, m-OH or p-Cl; and the salts, tautomers and optical isomers thereof; an effective amount of a second active ingredient selected from the group consisting of thidiazuron, diuron, ethephon, protoporphyrinogen oxidase (PPO) inhibitor herbicides; and, optionally, an adjuvant. The weight ratio of the first active ingredient to the second active ingredient is from about 1:0.05 to about 1:200.

According to a further aspect of the invention there are provided methods of inhibiting leaf regrowth in cotton comprising applying to cotton an effective amount of a guanidine compound having the formula (I):

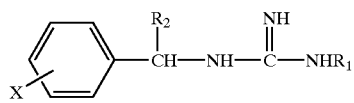

wherein $R_1$ is $NO_2$ or CN; $R_2$ is $CH_3$, $C_2H_5$ or $CF_3$; and X is hydrogen, o-F, m-F, p-F, m-$OCH_3$, m-OH or p-Cl, and the salts, tautomers and optical isomers thereof.

According to another aspect of the invention there are provided methods of inhibiting leaf regrowth in cotton comprising applying to cotton an effective amount of a first active ingredient selected from the group consisting of (+)isomers and (−)-isomers of guanidine compounds having the formula (I):

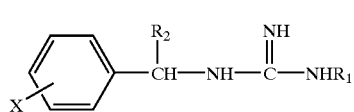

wherein $R_1$ is $NO_2$ or CN; $R_2$ is $CH_3$, $C_2H_5$ or $CF_3$; and X is hydrogen, o-F, m-F, p-F, m-$OCH_3$, m-OH or p-Cl; an effective amount of a second active ingredient selected from the group consisting of thidiazuron, diuron, ethephon, protoporphyrinogen oxidase (PPO) inhibitor herbicides; and, optionally, an adjuvant.

According to further aspects of the invention there are provided compositions comprising 1-(α-ethylbenzyl)-3-nitroguanidine and thidiazuron and compositions comprising (+)-1-(α-ethylbenzyl)-3-nitroguanidine and thidiazuron.

According to yet another aspect of the invention there are provided compositions comprising a first ingredient selected from the group consisting of substituted nitroguanidine and cyanoguanidine compounds of the formula (1):

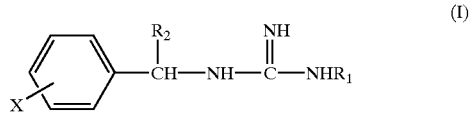

wherein $R_1$ is $NO_2$ or CN; $R_2$ is $CH_3$, $C_2H_5$, $CF_3$, n-$C_3H_7$, $CH_2OCH_3$ or $CH_2CH=CH_2$; X is hydrogen, o-F, m-F, p-F, m-$OCH_3$, m-OH or p-Cl; and the salts, tautomers and optical isomers thereof; and a second ingredient selected from the group consisting of herbicides, adjuvants, plant growth regulators, desiccants, boll opening compounds, pesticides, fertilizers and defoliants other than guanidine compounds having the formula (I). The second ingredient is present in an amount sufficient to enhance the defoliation and/or regrowth control activity of the first ingredient.

The methods and compositions of the invention of the invention are advantageous in that low levels of the guanidine compounds are required.

These and additional aspects, objects and advantages of the invention are more fully described in the following detailed description.

DETAILED DESCRIPTION

The present invention is directed to methods comprising the step of applying to plants, more particularly to the foliage of plants, a guanidine compound and a second ingredient selected from desiccants, defoliants other than guanidine compounds, boll opening compounds, herbicides, pesticides, adjuvants and combinations thereof. In a preferred embodiment, the plants are cotton plants, and the application of the first and second ingredients occurs prior to harvest.

The present invention is also directed to methods of controlling regrowth comprising the step of applying to plants, more particularly the foliage of plants, a guanidine compound. In a preferred embodiment, the plants are cotton plants, and the application of the guanidine compound occurs prior to harvest.

Suitable guanidine compounds include substituted nitroguanidine and cyanoguanidine compounds of the formula:

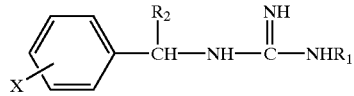

wherein $R_1$ is $NO_2$ or CN; $R_2$ is $CH_3$, $C_2H_5$, $CF_3$, n-$C_3H_7$, $CH_2OCH_3$ or $CH_2CH=CH_2$; X is hydrogen, o-F, m-F, p-F, m-$OCH_3$, m-OH or p-Cl; and the salts, tautomers and optical isomers thereof. In one embodiment the guanidine compound is selected from the group consisting of consisting of (+)-isomers, (−)-isomers and mixtures thereof of compounds having the formula (I):

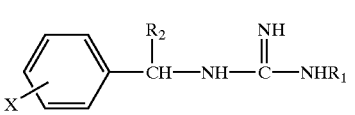

wherein $R_1$ is $NO_2$ or CN; $R_2$ is $CH_3$, $C_2H_5$ or $CF_3$; and X is hydrogen, o-F, m-F, p-F, m-$OCH_3$, m-OH or p-Cl. Preferably the guanidine compound is 1-(α-ethylbenzyl)-3-nitroguanidine, which exists in (+) and (−) isomeric forms.

More preferably the guanidine compound is (+)-1-(α-ethylbenzyl)-3-nitroguanidine.

Compositions in accordance with the present invention may comprise a second active ingredient, such as a herbicides, pesticides, growth regulators, boll openers fertilizers or defoliants other than the compounds of formula (I); or may comprise an adjuvant as a second ingredient. In one embodiment the compositions comprise both a second active ingredient and an adjuvant.

Suitable active ingredients include thidiazuron (N-phenyl-N'-1,2,3-thiadiazol-5-ylurea), diuron (N'-(3,4-dichlorophenyl)-N,N-dimethylurea), ethephon (2-chloroethyl)phosphonic acid), protoporphyrinogen oxidase (PPO) inhibitor herbicides. In one embodiment the second active ingredient is selected from the group consisting of thidiazuron, such as sold under the trade name Dropp®, diuron, and ethephon, such as sold under the trade name Prep®, preferably the second active ingredient is thidiazuron.

As used herein, "adjuvants" is intended to refer to ingredients which by themselves are not defoliants but which can enhance the activity of the defoliants active ingredient. Adjuvants include acidifying agents, buffering agents, defoamers, compatibility agents, conditioning agents, drift control agents, surfactants, penetrants, spreaders, stickers, wetting agents, and activators. In a preferred embodiment the adjuvant is selected from acidifying agents, buffering agents, activators, isopropylamine and mixtures thereof.

As used herein, acidifying agent refers to a material that can be added to spray mixtures to lower the pH, such as ammonium sulfate solution, while buffering agent refers to a material that, when contained in a solution, causes the solution to resist change in pH, such as a mixture of ammonium sulfate and dimethylpolysiloxane. As used herein, activator refers to a material that increases the biological efficacy of agrichemicals, such as crop oil concentrate.

In one embodiment the second ingredient is selected from the group consisting of thidiazuron, diuron, ethephon, protoporphyrinogen oxidase (PPO) inhibitor herbicides, acidifying agents, buffering agents, activators, isopropylamine, ammonium sulfate and mixtures thereof Generally the guanidine compound and the second ingredient are applied at levels sufficient to defoliate or inhibit regrowth of the plants. In one embodiment the second ingredient is applied at a level sufficient to increase the activity of the guanidine compound.

In one embodiment the weight ratio of the amount of guanidine compound applied to the plants to the amount of second ingredient applied to the plants is from about 1:0.05 to about 1:200. In one embodiment the weight ratio is from about 1:0.05 to about 1:100, preferably from about 1:0.05 to about 50. In another embodiment the weight ratio is from about 1:0.05 to about 1:10, preferably from about 1:0.05 to about 1:5, more preferably from about 1:0.05 to about 1:2.

In one embodiment of the invention the application rate of the guanidine compound is from about 0.03 to about 0.5, preferably from about 0.06 to about 0.25, lb/acre. The application rate of the second ingredient is from about 0.005 to about 10 lb/acre, from about 0.005 to about 5 lb/acre, from about 0.01 to about 5 lb/acre, or from about 0.01 to about 1 lb/acre.

Thidiazuron, generally has an application rate of from about 0.025 to about 0.5, preferably from about 0.05 to 0.2, lb/acre, while diuron, generally has, for cotton defoliation purpose, an application rate of from about 0.01 to about 0.5, preferably from about 0.025 to about 0.063, lb/acre and ethephon generally has an application rate of from about 0.25 to about 2.0, preferably from about 0.25 to about 1.5 lb/acre.

In one embodiment the guanidine compound and the second ingredient are applied sequentially at substantially the same time. As used herein, substantially the same time means the ingredients are generally applied to plants within about 24 hours of one another.

In another embodiment a treatment composition comprises both the guanidine compound and the second ingredient, and the compounds are applied to the plants simultaneously. The weight ratio of the guanidine compound to the second ingredient is from about 1:0.05 to about 1:200, from about 1:0.05 to about 1:100, from about 1:0.05 to about 50, from about 1:0.05 to about 1:10, from about 1:0.05 to about 1:5, or from about 1:0.05 to about 1:2.

In one embodiment the guanidine compound is 1-(α-ethylbenzyl)-3-nitroguanidine, more preferably, (+)-1-(α-ethylbenzyl)-3-nitroguanidine and the second active ingredient is thidiazuron. The weight ratio of the 1-(α-ethylbenzyl)-3-nitroguanidine to the thidiazuron is from about 1:0.05 to about 1:5, preferably from about 1:0.05 to about 1:2.

In one embodiment of the invention a defoliant composition comprises a first guanidine compound having the formula (I), a second active ingredient, and, optionally, an adjuvant. In one embodiment the adjuvant is selected from the group consisting of acidifying agents, buffering agents, defoamers, compatibility agents, conditioning agents, drift control agents, surfactants, penetrants, spreaders, stickers, wetting agents, and activators.

In one embodiment according to the invention a composition comprises the guanidine compound and an ingredient selected from extenders, crop oil concentrates, vegetable oil concentrates and/or surfactants. As used herein "extenders" is intended to include liquid solvents and/or solid carriers, and "surfactants" is intended to include emulsifiers and/or dispersants and/or foam formers. Preferred surfacantants are non-ionic surfactants.

Generally crop oil concentrates, vegetable oil concentrates and/or non-ionic surfactants are present in the composition at a level from about 0.1 to about 5%, preferably from about 0.5 to about 2%, by volume for applications of agrichemicals using ground equipment and at a level from about 5 to about 50% by volume for applications using aerial equipment. Suitable crop oil concentrates include blends of paraffinic petroleum oil and surfactants such as poly fatty acid esters and polyethyoxylated derivatives of fatty acid esters.

Suitable liquid solvents include water and organic solvents. Organic solvents include aromatic solvents, such as xylene, toluene or alkylnaphthalenes; chlorinated aromatics and chlorinated aliphatic hydrocarbons, such as chlorobenzenes, chloroethylenes or methylene chloride; aliphatic hydrocarbons, such as cyclohexane or paraffins, mineral and vegetable oils; alcohols, such as butanol or glycol, and also their ethers and esters; ketones, such as acetone, methyl ethyl ketone, methyl isobutyl ketone or cyclohexanone; and polar solvents, such as dimethylformamide and dimethyl sulphoxide. Suitable solid carriers include ground natural minerals and/or rocks, such as kaolins, clays, talc, chalk, quartz, attapulgite, montmorillonite or diatomaceous earth; ground synthetic minerals, such as finely divided silica, alumina and silicates; and granules of organic material, such as sawdust, coconut shells, maize cobs and tobacco stalks.

The composition may further comprise tackifiers and colorants Suitable tackifiers include carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids. Suitable colorants include inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The composition may be prepared by mixing the ingredient in any suitable order and manner. The ingredients may be in any suitable form, such as emulsifiable concentrates, wettable powders, or suspensions.

In one embodiment the composition is in the form of a liquid comprising from about 0.2% to about 2%, by volume, adjuvant. The composition may comprise the first ingredient at an amount sufficient to provide from about 0.06 to about 0.25 lb/acre of the guanidine compound when the composition is sprayed on plants.

In one embodiment of the invention the composition is provided in a liquid or dry concentrated form which is diluted prior to use, while in another embodiment the composition is provided in a ready-to-use form.

In one embodiment the composition is a liquid applied at a level of at least about 5, preferably at least about 15 gallons per acre. In one embodiment the composition is a liquid applied at a level of from about 5 to about 30, while in another embodiment the liquid is applied at a level from about 15 to about 30, gallons per acre. Typically aerial application uses less liquid than ground application.

Proper timing of defoliant application is within the skill of those in the art. Generally application of defoliants to cotton is determined based on factors such as the maturity of the cotton bolls and/or the percentage of the bolls which are open. Generally the guanidine compound and second active ingredients are applied when about 40 to about 100%, preferably from about 60 to about 90% of the bolls are open. Then crop is generally harvested after from about 5 to about 25, preferably after from 10 to about 15, days after application of defoliant.

EXAMPLES

Throughout the present specification, parts and percentages are by weight unless otherwise specified. The following examples are illustrative only and are not intended to limit the scope of the methods of the invention as defined by the claims.

American upland cotton was treated by spraying with the treatment chemicals set forth in Tables 1–3 and evaluated 10, 14 and 21 days after treatment. The cotton was treated when mature with about 65% open bolls when the crop canopy was open and some natural defoliation had begun.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

TABLE 1

Effects on Cotton Plants 10 Days After Treatment Application

| Treatment | Application Rate (lb/acre) | % Dead Leaves On Plants | % Dropped Leaves |
|---|---|---|---|
| untreated control | — | 0.0 | 23.3 |
| Def + Dropp + COC | Def = 0.75 Dropp = 0.05 | 25.0 | 73.3 |
| (+)/(−) EBNG + COC + | (+)/(−) EBNG = 0.25 | 3.3 | 87.3 |
| (+) EBNG + COC | (+) EBNG = 0.25 | 4.3 | 93.3 |
| (+) EBNG + COC | (+) EBNG = 0.19 | 5.3 | 90.7 |
| (+) EBNG + COC | (+) EBNG = 0.13 | 3.3 | 90.3 |
| (+) EBNG + COC | (+) EBNG = 0.13 | 3.7 | 90.0 |
| (+) EBNG + Dropp + COC | (+) EBNG = 0.06 Dropp = 0.05 | 10.0 | 83.7 |
| (+) EBNG + Dropp + NIS | (+) EBNG = 0.06 Dropp = 0.05 | 6.0 | 90.0 |
| (+) EBNG + Dropp + COC | (+) EBNG = 0.13 Dropp = 0.05 | 9.0 | 90.0 |
| (+) EBNG | (+) EBNG = 0.13 | 8.3 | 90.0 |

Def = Def-6 ®, S,S,S-tributyl phosphorotrithioate
Dropp = Dropp ®, thidiazuron
COC = crop oil concentrate
(+)/(−) EBNG = mix of (+) and (−) isomers of 1-(α-ethylbenzyl)-3-nitroguanidine
(+) EBNG = (+) isomer of 1-(α-ethylbenzyl)-3-nitroguanidine
NIS = non-ionic surfactant The data in Table 1 indicate that the application of a combination of 0.06 lb/acre (+) isomer of 1-(α-ethylbenzyl)-3-nitroguanidine and 0.05 lb/acre thidiazuron, a composition in accordance with the invention, resulted in a greater percentage of dropped leaves than a combination of 0.75 lb/acre S,S,S-tributyl phosphorotrithioate and 0.05 lb/acre thidiazuron. Thus, compositions in accordance with the present invention provide good defoliation even at low application levels of the active ingredient.

TABLE 2

Effects on Cotton Plants 14 Days After Treatment Application

| Treatment | Application Rate (lb/acre) | % Dead Leaves On Plants | % Dropped Leaves | % New Growth Leaves | % Open Fruits |
|---|---|---|---|---|---|
| untreated control | — | 0.7 | 56.7 | 0.0 | 93.3 |
| Def + Dropp + COC | Def = 0.75 Dropp = 0.05 | 21.7 | 76.7 | 0.0 | 97.0 |
| (+)/(−) EBNG + COC | (+)/(−) EBNG = 0.25 | 0.7 | 97.0 | 0.7 | 96.0 |
| (+) EBNG + COC | (+) EBNG = 0.25 | 1.3 | 97.7 | 0.0 | 96.7 |
| (+) EBNG + COC | (+) EBNG = 0.19 | 1.7 | 97.3 | 0.3 | 96.7 |

TABLE 2-continued

Effects on Cotton Plants 14 Days After Treatment Application

| Treatment | Application Rate (lb/acre) | % Dead Leaves On Plants | % Dropped Leaves | % New Growth Leaves | % Open Fruits |
|---|---|---|---|---|---|
| (+) EBNG + COC | (+) EBNG = 0.13 | 0.7 | 99.0 | 0.0 | 96.7 |
| (+) EBNG + COC | (+) EBNG = 0.13 | 1.7 | 97.7 | 0.0 | 96.3 |
| (+) EBNG + Dropp + COC | (+) EBNG = 0.06 Dropp = 0.05 | 9.3 | 90.0 | 0.0 | 96.3 |
| (+) EBNG + Dropp + NIS | (+) EBNG = 0.06 Dropp = 0.05 | 5.7 | 93.7 | 0.3 | 97.0 |
| (+) EBNG + Dropp + COC | (+) EBNG = 0.13 Dropp = 0.05 | 6.3 | 92.0 | 0.3 | 97.3 |
| (+) EBNG | (+) EBNG = 0.13 | 5.7 | 93.0 | 1.0 | 96.0 |

Def = Def-6 ®, S,S,S-tributyl phosphorotrithioate
Dropp = Dropp ®, thidiazuron
COC = crop oil concentrate
(+)/(−) EBNG = mix of (+) and (−) isomers of 1-($\alpha$-ethylbenzyl)-3-nitroguanidine
(+) EBNG = (+) isomer of 1-($\alpha$-ethylbenzyl)-3-nitroguanidine
NIS = non-ionic surfactant The data in Table 2 indicate that compositions in accordance with the present invention provide good defoliation and inhibit leaf regrowth even at low application levels of the active ingredient.

TABLE 3

Effects on Cotton Plants 21 Days After Treatment Application

| Treatment | Application Rate (lbs/acre) | % New Growth Leaves | % Open Fruits |
|---|---|---|---|
| untreated control | — | 4.0 | 95.3 |
| Def + +Dropp + COC | Def = 0.75 Dropp = 0.05 | 2.3 | 98.0 |
| (+)/(−) EBNG + COC | (+)/(−) EBNG = 0.25 | 2.3 | 96.7 |
| (+) EBNG + COC | (+) EBNG = 0.25 | 2.0 | 98.3 |
| (+) EBNG + COC | (+) EBNG = 0.19 | 2.7 | 97.7 |
| (+) EBNG + COC | (+) EBNG = 0.13 | 2.0 | 98 |
| (+) EBNG + COC | (+) EBNG = 0.13 | 3.0 | 97.0 |
| (+) EBNG + Dropp + COC | (+) EBNG = 0.06 Dropp = 0.05 | 1.7 | 98.0 |
| (+) EBNG + Dropp + NIS | (+) EBNG = 0.06 Dropp = 0.05 | 2.0 | 98.0 |
| (+) EBNG + Dropp + COC | (+) EBNG = 0.13 Dropp = 0.05 | 2.7 | 98.7 |
| (+) EBNG | (+) EBNG = 0.13 | 3.7 | 98.3 |

Def = Def-6 ®, S,S,S-tributyl phosphorotrithioate
Dropp = Dropp ®, thidiazuron
COC = crop oil concentrate
(+)/(−) EBNG = mix of (+) and (−) isomers of 1-($\alpha$-ethylbenzyl)-3-nitroguanidine
(+) EBNG = (+) isomer of 1-($\alpha$-ethylbenzyl)-3-nitroguanidine
NIS = non-ionic surfactant The data in Table 3 indicate that compositions in accordance with the present invention provide leaf regrowth inhibition after 21 days even at low application levels of the active ingredient.

Plots of American upland cotton planted in several states (Arkansas (AR), Mississippi (MS), Georgia (GA), Texas (TA), Arizona (AZ) and California (CA)) were treated by spraying with the treatment chemicals set forth in Tables 4–10 and evaluated 1 and 2 weeks after treatment for percent of defoliation. The cotton was treated when mature when the crop canopy was open and some natural defoliation had begun.

TABLE 4

Percent Defoliation EBNG + Dropp ®

| | | % defoliation 1 week after application | | % defoliation 2 weeks after application | |
|---|---|---|---|---|---|
| Trial # | Location (state) | EBNG 0.063 lb ai/ac + 1% COC | EBNG 0.063 + Dropp 0.05 lb ai/ac + 1% COC | EBNG 0.063 lb ai/ac + 1% COC | EBNG 0.063 + Dropp 0.05 lb ai/ac + 1% COC |
| 354-00-51 | AR | 78 | 79 | 96 | 96 |
| 355-00-51 | AR | 88 | 97 | 93 | 98 |
| bms-00-24 | MS | 83 | 89 | 87 | 96 |
| tga-00-17 | GA | 36 | 40 | 71 | 79 |
| Average | | 71 | 76 | 87 | 92 |

EBNG = 1-($\alpha$-ethylbenzyl)-3-nitroguanidine
Dropp = Dropp ®, thidiazuron
COC = crop oil concentrate

TABLE 5

Percent Defoliation EBNG + Ammonium Sulfate

| | | 1 week after application | | 2 weeks after application | |
|---|---|---|---|---|---|
| Trial # | Location (State) | EBNG 0.125 lb ai/ac + 1% COC | EBNG 0.125 lb ai/ac + 2% AMSUL + 1% COC | EBNG 0.125 lb ai/ac + 1% COC | EBNG 0.125 lb ai/ac + 2% AMSUL + 1% COC |
| bms-00-25 | MS | 79 | 90 | 95 | 99 |

EBNG = 1-($\alpha$-ethylbenzyl)-3-nitroguanidine
COC = crop oil concentrate
AMSUL = ammonium sulfate

TABLE 6

Percent Defoliation EBNG + Hasten ®

| | | 1 week after application | | 2 weeks after application | |
|---|---|---|---|---|---|
| Trial # | Location (state) | EBNG 0.125 lb ai/ac + 1% COC | EBNG 0.125 lb ai/ac + 1% Hasten | EBNG 0.125 lb ai/ac + 1% COC | EBNG 0.125 lb ai/ac + 1% Hasten |
| bms-00-26 | MS | 42 | 72 | 91 | 96 |
| tga-00-17 | GA | 41 | 43 | 76 | 81 |
| Average | | 42 | 57 | 84 | 89 |

EBNG = 1-(α-ethylbenzyl)-3-nitroguanidine
COC = crop oil concentrate
Hasten = Hasten ®, methylated seed oil and surfactants/emulsifiers

TABLE 7

Percent Defoliation EBNG + Diuron

| | | 1 week after application | | 2 weeks after application | |
|---|---|---|---|---|---|
| Trial # | Location (state) | EBNG 0.125 lb ai/ac + 1% COC | EBNG 0.125 + Diuron 0.025 lb. ai/ac + 1% COC | EBNG 0.125 lb ai/ac + 1% COC | EBNG 0.125 + Diuron 0.025 lb ai/ac + 1% COC |
| bms-00-23 | MS | 98 | 100 | 97 | 100 |
| bms-00-25 | MS | 79 | 73 | 95 | 93 |
| bms-00-26 | MS | 42 | 45 | 91 | 92 |
| tga-00-27 | GA | 36 | 40 | 85 | 79 |
| Average | | 64 | 65 | 92 | 91 |

EBNG = 1-(α-ethylbenzyl)-3-nitroguanidine
COC = crop oil concentrate

TABLE 8

Percent Defoliation EBNG + PPO herbicides

| | | % defoliation 1 week after application | | |
|---|---|---|---|---|
| Trial # | Location (state) | EBNG 0.125 lb ai/ac + 1% COC | EBNG 0.125 lb ai/ac + Aim 0.008 lb ai/ac + 1% COC | Aim 0.015 lb ai/ac + 1% COC |
| 354-00-51 | AR | 87 | 81 | 32 |
| 355-00-51 | AR | 93 | 89 | 48 |
| bms-00-23 | MS | 98 | 97 | 85 |
| bms-00-25 | MS | 79 | 79 | 42 |
| tga-00-27 | GA | 36 | 39 | 38 |
| Average | | 79 | 77 | 49 |

EBNG = 1-(α-ethylbenzyl)-3-nitroguanidine
COC = crop oil concentrate
Aim = carfentrazone-ethyl

TABLE 9

Percent Defoliation EBNG + PPO herbicides

| | | % defoliation 2 weeks after application | | |
|---|---|---|---|---|
| Trial # | Location (state) | EBNG 0.125 lb ai/ac + 1% COC | EBNG 0.125 + Aim 0.008 lb ai/ac + 1% COC | Aim 0.015 lb ai/ac + 1% COC |
| 354-00-51 | AR | 98 | 94 | 40 |
| 355-00-51 | AR | 95 | 86 | 51 |
| bms-00-23 | MS | 97 | 99 | 84 |
| bms-00-25 | MS | 95 | 94 | 52 |
| tga-00-27 | GA | 85 | 78 | 78 |
| Average | | 94 | 90 | 61 |

EBNG = 1-(α-ethylbenzyl)-3-nitroguanidine
COC = crop oil concentrate
Aim = carfentrazone-ethyl

TABLE 10

Percent Defoliation EBNG + Prep

| | | 1 week after application | | 2 weeks after application | |
|---|---|---|---|---|---|
| Trial # | Location (state) | EBNG 0.125 lb ai/ac + 1% COC | EBNG 0.125 + Prep 0.25 lb ai/ac + 1% COC | EBNG 0.125 lb ai/ac + 1% COC | EBNG 0.125 + Prep 0.25 lb ai/ac + 1% COC |
| 456-00-55 | TX | 50 | 70 | 94 | 95 |
| 456-00-56 | TX | 48 | 55 | 87 | 86 |
| 459-00-01 | TX | 64 | 73 | 83 | 85 |
| 458-00-01 | AZ | 22 | 58 | 65 | 84 |
| fca-00-16 | CA | 8 | 40 | 65 | 65 |

TABLE 10-continued

Percent Defoliation EBNG + Prep

| | | 1 week after application | | 2 weeks after application | |
|---|---|---|---|---|---|
| Trial # | Location (state) | EBNG 0.125 lb ai/ac + 1% COC | EBNG 0.125 + Prep 0.25 lb ai/ac + 1% COC | EBNG 0.125 lb ai/ac + 1% COC | EBNG 0.125 + Prep 0.25 lb ai/ac + 1% COC |
| fca-00-17 | CA | 33 | 53 | 60 | 85 |
| Average | | 37 | 58 | 76 | 83 |

EBNG = 1-(α-ethylbenzyl)-3-nitroguanidine
COC = crop oil concentrate
Prep = Prep ®, ethephon The data in Tables 1–10 indicate that compositions in accordance with the invention provide good defoliant activity.

Plots of American upland cotton planted in several states (Arkansas (AR), Mississippi (MS) and Georgia (GA)) were treated by spraying with the treatment chemicals set forth in Table 11 and evaluated 2 and 3 weeks after treatment for regrowth. The data in Table 11 indicate that compositions in accordance with the invention provide good regrowth control.

TABLE 11

Regrowth Control

| | | % Regrowth Control (2–3 weeks after application) | | | | |
|---|---|---|---|---|---|---|
| Trail # | Location (state) | Def 0.75 + Dropp 0.05 lb ai/ac + 1% COC | EBNG 0.187 lb ai/ac + 1% COC | EBNG 0.125 lb ai/ac + 1% COC | Dropp 0.1 lb ai/ac + 1% COC | Def 1.0 lb ai/ac + 1% COC |
| 354-00-51 | AR | 39 | 43 | 53 | | |
| 355-00-51 | AR | 89 | 84 | 76 | | |
| bms-00-24 | MS | 78 | 67 | 68 | | |
| 354-99-30 | AR | 98 | 98 | 98 | | |
| bms-99-20 | MS | 70 | 82 | 83 | 87 | 40 |
| bms-99-22 | MS | 58 | 75 | 50 | 40 | 10 |
| 356-99-50 | GA | 30 | 30 | 39 | | |
| 356-99-51 | GA | 33 | 33 | 33 | | |
| tga-99-12 | GA | 83 | 86 | 88 | | |
| tga-99-13 | GA | 83 | 96 | 95 | | |
| Average | | 66 | 69 | 68 | 64 | 25 |

EBNG = 1-(α-ethylbenzyl)-3-nitroguanidine
Def = Def-6 ®, S,S,S-tributyl phosphorotrithioate
Dropp = Dropp ®, thidiazuron
COC = crop oil concentrate Additional embodiments and modifications within the scope of the claimed invention will be apparent to one of ordinary skill in the art. Accordingly, the scope of the present invention shall be considered in terms of the following claims, and is understood not to be limited to the details of the methods described in the specification.

What is claimed is:

1. A method of defoliating plants comprising applying to plants (1) an effective amount of a first active ingredient selected from the group consisting of (+)-isomers of substituted nitroguanidine and cyanoguanidine compounds of the formula (I):

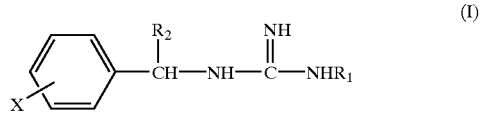

wherein $R_1$ is $NO_2$ or CN; $R_2$ is $CH_3$, $C_2H_5$, or $CF_3$; X is hydrogen, o-F, m-F, p-F, m-$OCH_3$, m-OH or p-Cl; and the salts and tautomers thereof;

(2) an effective amount of a second active ingredient selected from the group consisting of thidiazuron, diuron, ethephon, protoporphyrinogen oxidase inhibitor herbicides; and (3) optionally, an adjuvant;

wherein the weight ratio of the first active ingredient to the second active ingredient is from about 1:0.05 to about 1:200.

2. A method according to claim 1, wherein the application rate of the first active ingredient is from about 0.03 to about 0.5 lbs/acre and the application rate of the second active ingredient is from about 0.005 to about 10 lbs/acre.

3. A method according to claim 1, wherein the first active ingredient is (+)-1-(α-ethylbenzyl)-3-nitroguanidine.

4. A method according to claim 3, comprising applying to plants (+)-1-1-(α-ethylbenzyl)-3-nitroguanidine at a rate of from about 0.03 to about 0.5 lbs/acre and the second active ingredient at a rate of from about 0.005 to about 10 lb/acre.

5. A method according to claim 1, wherein the plant is cotton.

6. A method according to claim 1, comprising applying to plants an effective amount of a composition comprising (+)-1-(α-ethylbenzyl)-3-nitroguanidine and thidiazuron.

7. A method of inhibiting leaf regrowth in cotton comprising applying to cotton
   (1) an effective amount of a first active ingredient selected from the group consisting of (+)-isomers of guanidine compounds having the formula:

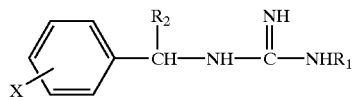

wherein $R_1$ is $NO_2$ or CN; $R_2$ is $CH_3$, $C_2H_5$ or CF; and X is hydrogen, o-F, in-F, p-F, m-OCH$_3$, m-OH or p-Cl;

(2) an effective amount of a second active ingredient selected from the group consisting of thidiazuron, diuron, ethephon, protoporphyrinogen oxidase inhibitor herbicides, ammonium sulfate and combinations thereof; and (3) optionally, adjuvant.

8. A method according to claim 7, wherein the first active ingredient is (+)-1-(α-ethylbenzyl)-3-nitroguanidine and the second active ingredient is thidiazuron and further wherein the weight ratio of 1-(α-ethylbenzyl)-3-nitroguanidine and thidiazuron from about 1:0.05 to about 1:200.

* * * * *